United States Patent [19]

Katsube et al.

[11] 4,316,028
[45] Feb. 16, 1982

[54] PROCESS FOR PRODUCING EBURNANE DERIVATIVES

[75] Inventors: Junki Katsube, Toyonaka; Keiichi Ono, Osaka; Hajime Kawakami, Takarazuka, all of Japan

[73] Assignee: Sumitomo Chemical Company, Limited, Osaka, Japan

[21] Appl. No.: 93,606

[22] Filed: Nov. 13, 1979

[30] Foreign Application Priority Data

Nov. 20, 1978 [JP] Japan ............................... 53-143841
Jan. 24, 1979 [JP] Japan ............................... 54-7482
Jan. 25, 1979 [JP] Japan ............................... 54-7849

[51] Int. Cl.³ ........................................... C07D 461/00
[52] U.S. Cl. ........................................... 546/51; 424/246; 546/70
[58] Field of Search ......................... 546/51; 424/256

[56] References Cited

U.S. PATENT DOCUMENTS

| | | | |
|---|---|---|---|
| 3,830,823 | 8/1974 | Castaigne | 546/51 |
| 3,925,393 | 12/1975 | Hertaux et al. | 546/51 |
| 3,937,709 | 2/1976 | Sevenet et al. | 546/51 |
| 4,035,370 | 7/1977 | Lörincz et al. | 546/51 |
| 4,057,550 | 11/1977 | Szantay et al. | 546/51 |
| 4,190,658 | 2/1980 | Warnant et al. | 424/256 |

FOREIGN PATENT DOCUMENTS

| | | | |
|---|---|---|---|
| 2115718 | 10/1971 | Fed. Rep. of Germany | 546/51 |
| 2085630 | 12/1971 | France | 424/256 |
| 1382609 | 2/1975 | United Kingdom | 546/51 |
| 1402085 | 8/1975 | United Kingdom | 546/51 |

OTHER PUBLICATIONS

Loerincz, et al., Chemical Abstracts, vol. 79, 18934y (1973).
Noller, Chemistry of Organic Compounds, 3rd ed., W. B. Saunders Co., Philadelphia, (1965), pp. 148-150.
Reagents for Organic Synthesis, Fieser, et al., John Wiley & Sons, New York, (1967) pp. 617-618.

*Primary Examiner*—Donald G. Daus
*Assistant Examiner*—Diana G. Rivers
*Attorney, Agent, or Firm*—Stevens, Davis, Miller & Mosher

[57] ABSTRACT

A compound of the formula:

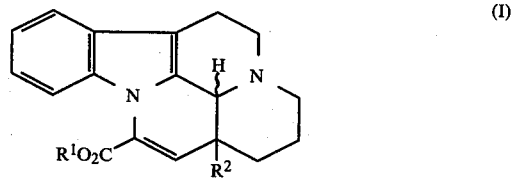

(I)

wherein $R^1$ is a $C_1$–$C_6$ alkyl group and R is a hydrogen atom or a $C_1$–$C_6$ alkyl group, and their salts, which are useful as cerebral vasodilator; and a compound of the formula:

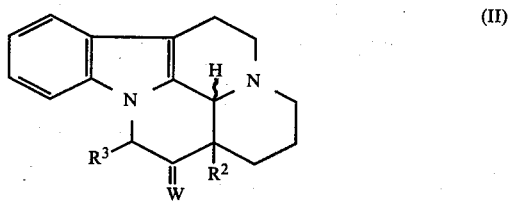

(II)

wherein $R^2$ is a hydrogen atom or a $C_1$–$C_6$ alkyl group, $R^3$ is a hydrogen atom or the formula: $-CO_2R^1$ ($R^1$ is a $C_1$–$C_6$ alkyl group) and W is an oxygen atom, an imino group or

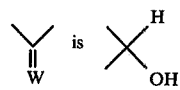

but not an imino group in case that $R^3$ is a hydrogen atom, which are intermediates of the compound (I), useful per se as cerebral vasodilator and/or antihypertensive agents.

12 Claims, No Drawings

PROCESS FOR PRODUCING EBURNANE DERIVATIVES

This invention relates to an improved process for producing apovincaminic acid esters and their salts, which are known to be useful as cerebral vasodilator, to their novel trans isomers, and to novel eburnane derivatives which are intermediates in the said process and useful per se as cerebral vasodilator and/or antihypertensive agents.

The said apovincaminic acid esters and their trans isomers are representable by the formula:

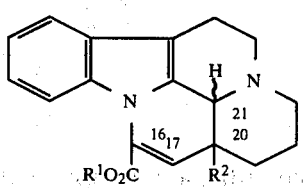

[I]

wherein $R^1$ is a $C_1$–$C_6$ alkyl group and $R^2$ is a hydrogen atom or a $C_1$–$C_6$ alkyl group.

The said eburnane derivatives are representable by the formula:

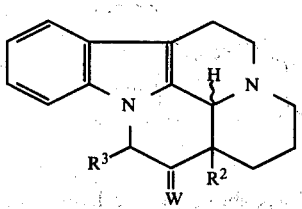

[II]

wherein $R^2$ is as defined above and W is an oxygen atom, an imino group or

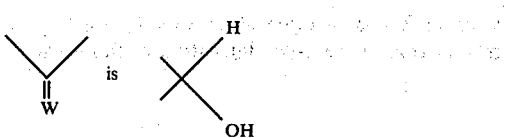

and $R^3$ is a hydrogen atom or the formula: $-CO_2R^1$ (wherein $R^1$ is as defined above), but W does not mean an imino group in case that $R^3$ is a hydrogen atom. Some of the apovincaminic acid esters of the formula [$I_A$]:

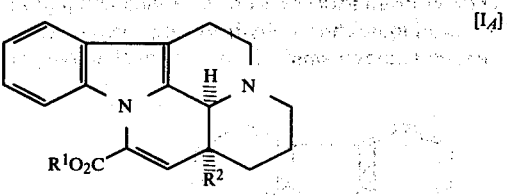

[$I_A$]

wherein $R^1$ and $R^2$ are each as defined above are known. For instance, with respect to the formula [$I_A$], those in which $R^1$ is a $C_2$–$C_6$ alkyl group and $R^2$ is an ethyl group are disclosed in the literature [cf. Hungarian Pat. No. 2251/71].

In the significations as defined above, a $C_1$–$C_6$ alkyl group includes methyl, ethyl, n-propyl, isopropyl, n-butyl, t-butyl, n-pentyl and n-hexyl. The term "trans" is meant that the substituent [$R^2$] at C-20 is trans to the hydrogen atom at C-21 as shown by the following figure.

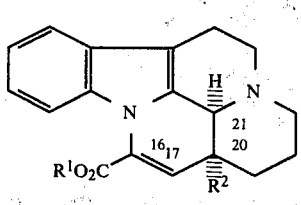

[$I_A$]
Cis

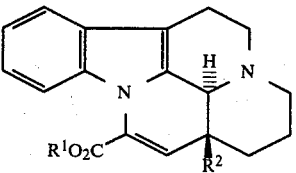

[$I_B$]
Trans

Animal tests have revealed that the apovincaminic acid ester [$I_A$], its trans isomer [$I_B$] and the eburnane derivative [II] have various pharmacological activities. Particularly, these derivatives show a cerebral vasodilating activity and/or an antihypoxic activity.

Therefore they are therapeutically useful to treat cerebral arteriosclerosis, senile mental indolence and the results of cerebral insufficiency.

According to the present invention, the apovincaminic acid ester [$I_A$] and its trans isomer [$I_B$] can be prepared from the corresponding ketoester of the formula:

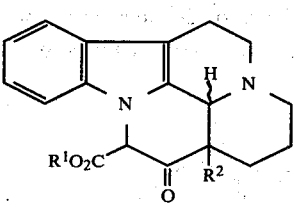

[$II_A$]

wherein $R^1$ and $R^2$ are each as defined above, by reduction to give the hydroxyester of the formula:

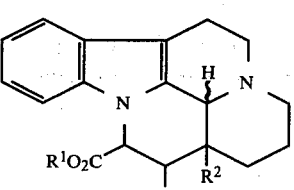

[$II_B$]

wherein $R^1$ and $R^2$ are each as defined above, followed by dehydration.

The ketoester [$II_A$] is novel and can be advantageously prepared by hydrolysis of the corresponding iminoester of the formula:

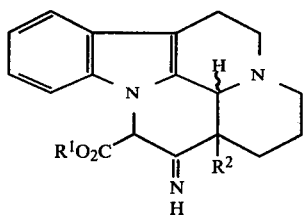

[II_C]

wherein $R^1$ and $R^2$ are each as defined above, or prepared by the reaction of the ketone derivative of the formula:

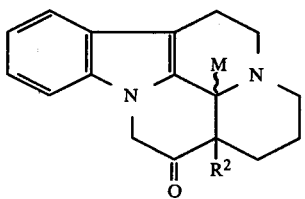

[II_D]

with a dialkylcarbonate.

The iminoester [II_C] can be produced advantageously by the reaction of an amido derivative of the formula:

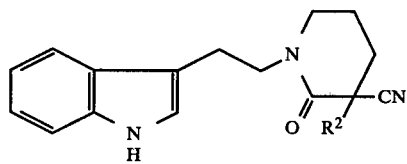

[III]

wherein $R^2$ is as defined above with a dehydrolyzing agent (e.g. phosphorus pentoxide, phosphorus oxychloride), followed by reduction to give a cyano derivative of the formula:

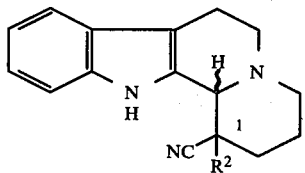

[IV]

wherein $R^2$ is as defined above, followed by reaction with a halogenoacetic acid ester of the formula:

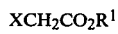 XCH$_2$CO$_2$R$^1$ [V]

wherein X is an halogen atom and $R^1$ is as defined above. When the cyano derivative [IV] is an isomeric mixture it can be separated by column chromatography to give the cis [IV_A] or the trans [IV_B], and if necessary, the trans [IV_B] can be converted to the corresponding cis [IV_A].

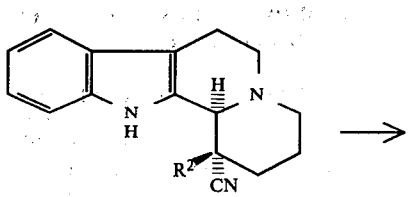

[IV_B]

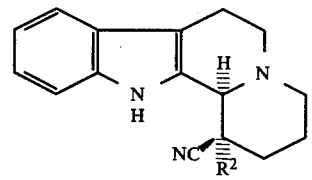

[IV_A]

The ketone derivative [II_D], which is also novel, can be produced by hydrolysis of the esters [II_A, II_C], followed by decarboxylation, by decarboalkoxylation of the keto ester [II_A] or by the reaction of an amido derivative of the formula:

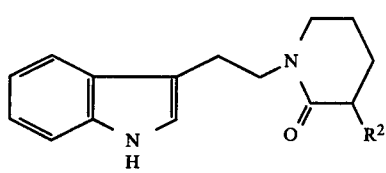

[VI]

wherein $R^2$ is as defined above, with a halogenoacetic acid ester of the formula:

 XCH$_2$CO$_2$R$^4$ [VII]

wherein X is a halogen atom and $R^4$ is a $C_1$–$C_6$ alkyl group, to give the ester derivative of the formula:

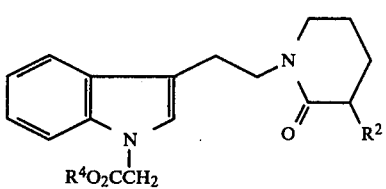

[VIII]

wherein $R^2$ and $R^4$ are each as defined above, followed by reaction with a dehydrolyzing agent to give the corresponding enamine derivative of the formula:

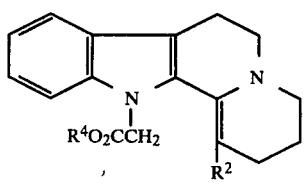

[IX]

wherein $R^2$ and $R^4$ are each as defined above, followed by heating without solvent and subsequent hydrogenation employing a platinum or a palladium catalyst. The ketone derivative [II_D] can be easily converted to the corresponding alcohol derivative by the reaction of the former with a reducing agent.
The sequence of the steps from the amide derivatives [III, VI] through the eburnane derivatives [II$_A$, II$_B$, II$_C$, II$_D$] to the apovincaminic acid ester [I$_A$] or its isomer [I$_B$] as stated above may be represented by the following schema:
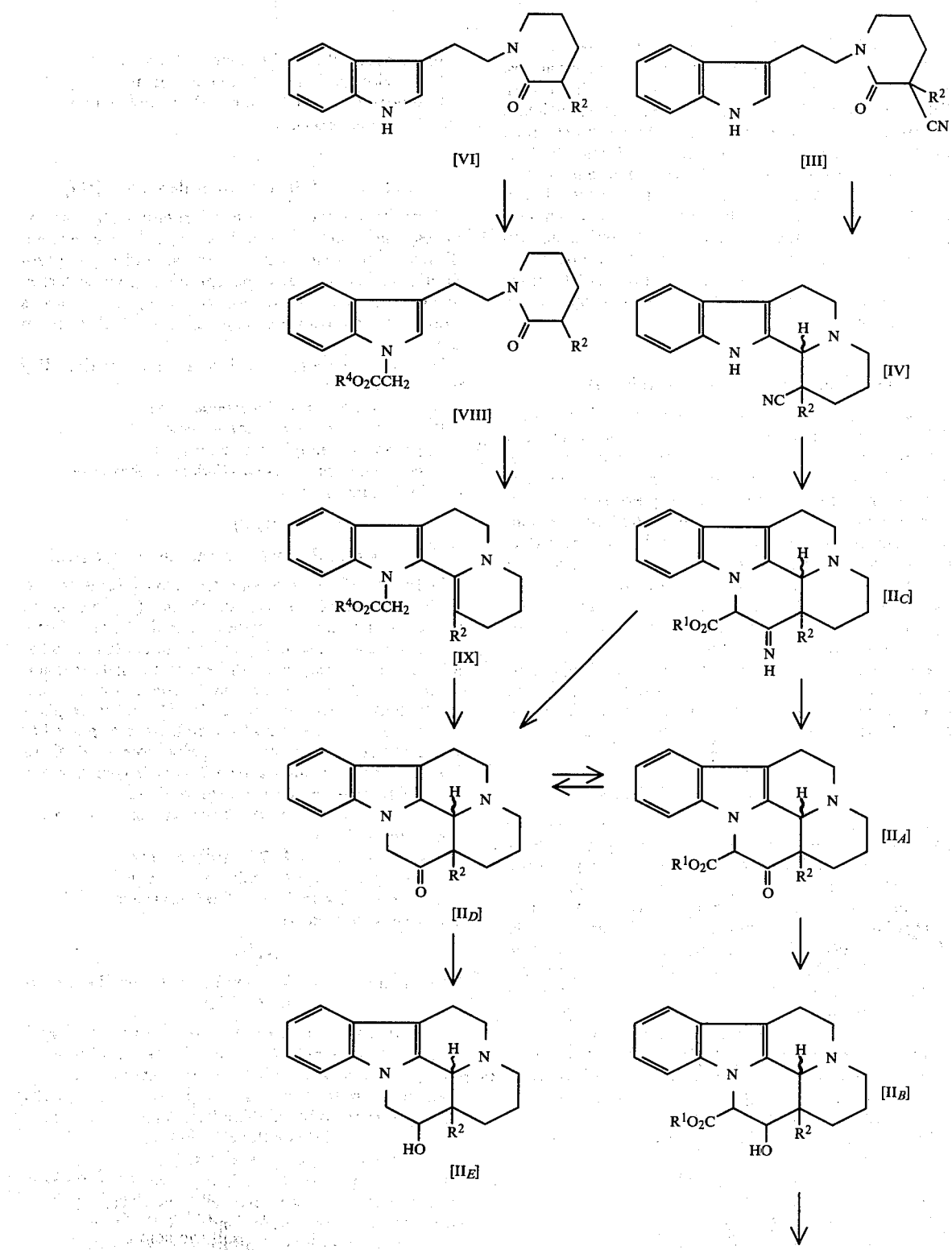

-continued

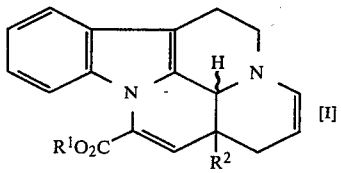

wherein $R^1$, $R^2$ and $R^4$ are each as defined above.

For the preparation of pharmaceutical compositions, they may be mixed with carriers, diluents, lubricants, fillers and/or binders such as lactose, sucrose, calcium phosphate, starch, talcum, casein, magnesium stearate, methyl cellulose, polyglycols, tragacanth and the like, sometimes together with stabilizers and emulsifying agents. The resulting mixture may be processed in a usual manner to form tablets, capsules, pills, ampules and the like. The usual oral dosage of the active ingredient is between about 5 mg and about 100 mg daily.

The process of the present invention will be illustrated below in detail according to the sequence of the reaction steps.

STEP 1

Production of the cyano derivative [IV].

The reaction of the amide derivative [III] with a dehydrolyzing agent is usually carried out in an inert solvent at a temperature range of from room temperature to the refluxing temperature of the reaction system, and a higher temperature is generally preferred. Examples of the inert solvent include aromatic hydrocarbons (e.g. benzene, toluene) and acetonitrile. For the reduction of the imino derivative obtained above, various reducing agents and systems are adopted such as treatment with a metal (e.g. zinc, iron) or its salt in the presence of an acid (e.g. hydrochloric acid, acetic acid) or metal hydride (e.g. sodium borohydride) reduction.

If necessary, the trans cyano derivative [$IV_B$] can be readily converted into the corresponding cis [$IV_A$] by reaction with an acid (e.g. hydrochloric acid, hydrobromic acid, phosphoric acid) at above 50° C.

STEP 2

Production of the imino ester derivative [$II_C$].

The cyano derivative [IV] can be converted into the corresponding imino ester derivative [$II_C$] by the reaction of the former with the halogenoacetic acid ester [e.g. chloroacetic acid ester, bromoacetic acid ester, iodoacetic acid ester] in the presence of an alkali in an inert solvent at a temperature range of from 10° C. to 70° C. As the alkali, there may be used for example alkali metal or alkaline earth metal alkoxide (e.g. sodium alkoxide, potassium alkoxide), an alkali metal hydride (e.g. sodium hydride, potassium hydride) or an alkali metal amide (e.g. sodium amide). Examples of the inert solvent include ethers (e.g. diethylether, tetrahydrofuran), aromatic hydrocarbons (e.g. benzene, toluene) and aprotic polar solvents (e.g. dimethylformamide dimethylacetamide, dimethyl sulfoxide).

Specific examples of the imino ester derivative [$II_C$] are as follows:
16-methoxycarbonyl-17-iminoeburnane
16-ethoxycarbonyl-17-iminoeburnane
16-propoxycarbonyl-17-iminoeburnane
16-butoxycarbonyl-17-iminoeburnane
16-pentoxycarbonyl-17-iminoeburnane
16-hexyloxycarbonyl-17-iminoeburnane
16-ethoxycarbonyl-17-imino-20-deethyleburnane
and these trans isomers.

STEP 3

Production of the keto ester derivative [$II_A$].

Hydrolysis of the imino ester derivative [$II_C$] into the corresponding keto ester derivative [$II_A$] can be accomplished by treatment with a mineral acid (e.g. hydrochloric acid, sulfuric acid, phosphoric acid) in water, an alkanol (e.g. metanol, ethanol, propanol) or an aqueous alkanol at a temperature range of from 0° C. to room temperature.

Specific examples of the keto ester derivative [$II_A$] are as follows:
16-methoxycarbonyl-17-oxoeburnane
16-ethoxycarbonyl-17-oxoeburnane
16-propoxycarbonyl-17-oxoeburnane
16-ethoxycarbonyl-17-oxo-20-deethyleburnane
and these trans isomers.

STEP 4

Production of the hydroxy ester derivative [$II_B$].

Reduction of the keto ester derivative [$II_A$] is carried out in an inert solvent such as alkanol (e.g. methanol, ethanol, isopropanol), aqueous alkanol, dimethylformamide containing alkanol, ethylacetate containing alkanol. As the reducing agent, there may be used for example metal hydride (e.g. sodium borohydride, calcium borohydride), palladium on charcoal, nickel or platinum oxide. The metal hydride reduction is peferably conducted at a temperature range of from $-10°$ C. to room temperature, and the catalytic hydrogenation at a range of from room temperature to 70° C.

Specific examples of the hydroxy ester derivative [$II_B$] are as follows:
16-methoxycarbonyl-17-hydroxyeburnane
16-ethoxycarbonyl-17-hydroxyeburnane
16-propoxycarbonyl-17-hydroxyeburnane
and these trans isomers.

STEP 5

Production of the apovincaminic acid ester [$I_A$] and its isomer [$I_B$].

Dehydration of the hydroxy ester derivative [$II_B$] is carried out in the presence of an acid or an alkali in an inert solvent such as alkanol (e.g. metanol, ethanol), aromatic hydrocarbons (e.g. benzene, toluene, xylene), dimethylformamide or dimethylacetamide at a temperature range of from room temperature to the refluxing temperature of the reaction system.

Examples of the suitable alkali are metal hydride (e.g. sodium hydride, calcium hydride), metal amide, metal alkoxide and triethylamine, and it is preferable to use sulfuric acid or P-toluenesulfuric acid as the acid.

Specific examples of the apovincaminic acid ester [I$_A$] and its isomer [I$_B$] are as follows:
ethyl apovincaminate
methyl apovincaminate
propyl apovincaminate
butyl apovincaminate
pentyl apovincaminate
hexyl apovincaminate
20-deethyl ethylapovincaminate
and these trans isomers.

STEP 6

Production of the ester derivative [VIII].

The reaction of the amide derivative [VI] with the halogenoacetic acid ester derivative [VII] is usually carried out in the presence of an alkali in an inert solvent (e.g. dimethylformamide) at a temperature range of from 10° C. to 50° C. Examples of the alkali include an alkali metal hydride (e.g. sodium hydride), an alkali metal alkoxide (e.g. sodium alkoxide) and an alkali metal amide (e.g. sodium amide).

STEP 7

Production of the enamine derivative [IX].

The ester derivative [VIII] can be converted into the corresponding enamine derivative [IX] by the reaction of the former with a dehydrolyzing agent (e.g. phosphorus pentoxide, phosphorus oxychloride) in an inert solvent (e.g. acetonitrile, benzene, toluene) at the refluxing temperature.

STEP 8

Production of the ketone derivative [II$_D$] from the enamine derivative [IX].

The enamine derivative [IX] can be converted into the corresponding ketone derivative [II$_D$] by heating without solvent, followed by hydrogenation employing a platinum or a palladium catalyst at room temperature.

STEP 9

The production of the ketone derivative [II$_D$] from the iminoester derivative [II$_C$] or the ketoester derivative [II$_A$].

The iminoester or ketoester derivative can be converted into the corresponding ketone derivative [II$_D$] by the reaction of the former in the presence of an acid (e.g. hydrochloric acid, sulfuric acid, phosphoric acid) in an inert solvent (e.g. H$_2$O, alkanol, aqueous alkanol, acetic acid) at above 0° C.

The ketone derivative [II$_D$] can be also obtained from the ketoester derivative [II$_A$] by the reaction of II$_A$ with an alkali metal halide (e.g. lithium iodide) in an inert solvent (e.g. dimethyl sulfoxide) at a temperature range of from 70° C. to 150° C.

Specific examples of the ketone derivative [II$_D$] are as follows
17-ketoeburnane
17-keto-20-deethyl eburnane
and these trans isomers.

STEP 10

The production of the ketoester derivative [II$_A$] from the ketone derivative [II$_D$].

The ketone derivative [II$_D$] can be converted into the corresponding ketoester derivative [II$_A$] by the reaction of the former with a dialkyl carbonate (e.g. diethyl carbonate) in the presence of an alkali (e.g. sodium hydride, sodium alkoxide, butyl lithium) in an inert solvent (e.g. benzene, toluene, tetrahydrofuran) at a temperature range of from room temperature to the refluxing temperature of the reaction system.

STEP 11

The production of the alcohol derivative [II$_E$].

The ketone derivative [II$_D$] can be converted into the corresponding alcohol derivative [II$_E$] by the reaction of the former with reducing agent in an inert solvent (e.g. H$_2$O, alkanol, aqueous alkanol) at a temperature range of from 0° to room temperature.

As the reducing agent, there may be used for example metal hydride (e.g. sodium borohydride, calcium borohydride), palladium on charcoal, nickel or platinum oxide.

The thus prepared apovincaminic acid ester [I$_A$], its stereo isomer [I$_B$] or eburnane derivative [II] can be readily converted into its inorganic or organic acid addition salts by a conventional procedure.

Practical and presently preferred embodiments of the present invention are illustratively shown in the following Examples, which are not intended to limit the scope of the invention thereto.

EXAMPLE 1

A mixture of 0.9 g of 1-[2-(indole-3-yl)ethyl]-3-cyano-3-ethyl-2-piperidone, 8.2 ml of phosphorus oxychloride and 30 ml of acetonitrile was heated under refluxing for 20 hours. After cooling, the reaction mixture was concentrated under reduced pressure. The residual oil was dissolved in methanol and allowed to react with sodium borohydride. The reaction mixture was diluted with water and extracted with ethylacetate. The extracts were washed with water; dried over anhydrous sodium sulfate, concentrated under reduced pressure and crystallized from methanol to give trans 1-cyano-1-ethyl-1,2,3,4,6,7,12,12b-octahydroindolo[2,3-a]quinolizine, M.P. 139°–141° C.

EXAMPLE 2

A mixture of 4.5 g of 1-[2-(indole-3-yl)ethyl]-3-cyano-3-ethyl-2-piperidone, 60 ml of phosphorus oxychloride and 60 ml of acetonitrile was heated under refluxing for 7.5 hours. After cooling, the reaction mixture was concentrated under reduced pressure and dissolved in 100 ml of glacial acetic acid. To this solution was added zinc powder at 80° C. to 85° C. After warming for an additional 30 minutes, the precipitate was filtered off, then washed with ethylacetate and water. The combined filtrate and washing were made alkaline and extracted with ethyl acetate. The ethyl acetate layer was washed with water, dried over anhydrous sodium sulfate, concentrated under reduced pressure and chromatographed on silica gel to affored cis 1-cyano-1-ethyl-1,2,3,4,6,7,12,12b-octahydroindolo[2,3-a]quinolizine, M.P. 231°–233° C. and its trans isomer, M.P. 139°–141° C.

EXAMPLE 3

A mixture of 1 g of trans 1-cyano-1-ethyl-1,2,3,4,6,7,12,12b-octahydroindolo[2,3-a]quinolizine and 50 ml of hydrochloric acid (35%) was heated under refluxing for 2 hours. After cooling, the reaction mixture was diluted with water, made alkaline and extracted with ethyl acetate. The ethyl acetate layer was washed with water, dried over anhydrous sodium sulfate and concentrated under reduced pressure. The residual solid was recrystallized from methanol to give cis 1-cyano-1-ethyl-1,2,3,4,6,7,12,12b-octahydroindolo[2,3-a]quinolizine, M.P. 231°–233° C.

EXAMPLE 4

To a solution of 0.25 g of trans 1-cyano-1-ethyl-1,2,3,4,6,7,12,12b-octahydroindolo[2,3-a]quinolizine in 5 ml of dimethylformamide was added in portions 0.1 g of sodium hydride (65%) at room temperature. After cooling, 0.25 g of ethyl chloroacetate was added and the mixture was stirred for additional 20 minutes. The reaction mixture was poured into water and extracted with ethyl acetate. The ethyl acetate layer was washed with water, dried over anhydrous sodium sulfate, concentrated under reduced pressure and crystallized from methanol to give trans 16-ethoxycarbonyl-17-iminoeburnane, M.P. 152°–157.5° C.

EXAMPLE 5

In a similar manner to Example 4, 16-ethoxycarbonyl-17-iminoeburnane was obtained, M.P. 148°–150° C.

EXAMPLE 6

A mixture of 2 g of trans 16-ethoxycarbonyl-17-iminoeburnane, 30 ml of hydrochloric acid (35%), 70 ml of water and 70 ml of ethanol was stirred for 2 hours at room temperature. The reaction mixture was poured into water, made alkaline and extracted with ethyl acetate. The ethyl acetate layer was washed with water, dried over anhydrous sodium sulfate, concentrated under reduced pressure and chromatographed on silica gel to afford trans 16-ethoxycarbonyl-17-oxoeburnane, M.P. 130°–131.5° C.

EXAMPLE 7

In a similar manner to Example 6, 16-ethoxycarbonyl-17-oxoeburnane was obtained, M.P. 139°–142.5° C.

EXAMPLE 8

To a solution of 0.3 g of trans 16-ethoxycarbonyl-17-oxoeburnane in 50 ml of ethanol was added in portions 0.5 g of sodium borohydride at room temperature. After stirring for 20 minutes, the reaction mixture was poured into water and extracted with ethyl acetate. The ethyl acetate layer was washed with water, dried over anhydrous sodium sulfate, concentrated under reduced pressure and chromatographed on silica gel to afford trans-16-ethoxycarbonyl-17-hydroxyeburnane, brownish oil,
NMR $\delta$(CDCl$_3$): 0.87 ppm (3H), 1.3 ppm (3H),
IR $\nu_{cm-1}^{film}$: 1720–1740 cm$^{-1}$.

EXAMPLE 9

To a solution of 0.8 g of trans 16-ethoxycarbonyl-17-oxoeburnane in 100 ml of methanol was added in portions 3.2 g of sodium borohydride under cooling. The reaction mixture was poured into water and extracted with ethyl acetate. The ethyl acetate layer was washed with water, dried over anhydrous sodium sulfate, concentrated under reduced pressure and crystallized from isopropylether to give trans 16-ethoxycarbonyl-17-hydroxyeburnane, M.P. 190°–192° C.,
NMR $\delta$(CDCl$_3$): 0.81 ppm (3H), 1.1 ppm (3H),
which was corresponded to the diastereoisomer of the compound obtained in Example 8.

EXAMPLE 10

To a solution of 0.3 g of 16-ethoxycarbonyl-17-oxoeburnane in 30 ml of ethanol was added in portions 2 g of sodium borohydride at room temperature and then the reaction mixture was poured into water and extracted with ethyl acetate. The ethyl acetate layer was washed with water, dried over anhydrous sodium sulfate and concentrated to give brownish oil of 16-ethoxycarbonyl-17-hydroxyeburnane,
IR $\nu_{cm-1}^{film}$: 1720–1740 cm$^{-1}$.
To a solution of the crude oil of 16-ethoxycarbonyl-17-hydroxyeburnane obtained above in 50 ml of toluene was added in portions 0.3 g of sodium hydride (65%) at room temperature. After refluxing for 30 minutes, the reaction mixture was poured into water and extracted with ethyl acetate. The ethyl acetate layer was washed with water, dried over anhydrous sodium sulfate, concentrated under reduced pressure and chromatographed on silica gel to give ethyl apovincaminate
IR $\nu_{cm-1}^{film}$: 1720 cm$^{-1}$
NMR $\delta$(CDCl$_3$): 1.0 ppm, 1.35, 4.48, 6.18.

EXAMPLE 11

To a solution of 0.5 g of 16-ethoxycarbonyl-17-oxoeburnane in 50 ml of ethanol was added in portions 1.0 g of sodium borohydride at −10° C.–0° C. After stirring for 25 minutes, the reaction mixture was poured into water and extracted with ethyl acetate. The ethyl acetate layer was washed with water, dried over anhydrous sodium sulfate, concentrated under reduced pressure and chromatographed on silica gel to give two diastereoisomers of 16-ethoxycarbonyl-17-hydroxyeburnane,
Fraction 1: NMR $\delta$(CDCl$_3$):
 1.03 ppm (3H, t)
 1.32 ppm (3H, t)
 4.23 ppm (1H, d)
 4.53 ppm (1H, d)
Fraction 2: NMR $\delta$(CDCl$_3$):
 0.93 ppm (3H, t)
 1.37 ppm (3H, t)
 4.32 ppm (1H, d)
 4.85 ppm (1H, d).

EXAMPLE 12

A mixture of 0.3 g of 16-ethoxycarbonyl-17-oxoeburnane, 1 g of hydrochloric acid (35%) and 20 g of water was heated under refluxing for 20 minutes. After cooling, the reaction mixture was poured into water and made alkaline. The precipitated crystals were collected by filtration and the crude crystals were chromatographed on silica gel to give 17-oxoeburnane, M.P. 106°–116° C.

EXAMPLE 13

A mixture of 0.15 g of trans 16-ethoxycarbonyl-17-iminoeburnane and hydrochloric acid (35%) was allowed to react on standing for 19 hours, and then poured into water, made alkaline, and extracted with ethyl acetate. The ethyl acetate layer was washed with water, dried over anhydrous sodium sulfate, concentrated under reduced pressure and crystallized from methanol to give trans 17-oxoeburnane, M.P. 150°–152° C.

EXAMPLE 14

A mixture of 14.5 g of 1-[2-(1-ethoxycarbonylmethylindole-3-yl)ethyl]-3-ethyl-2-piperidone, 30 ml of phosphorus oxychloride and 200 ml of acetonitrile was heated under refluxing for 1.5 hours. After cooling, the reaction mixture was concentrated, made alkaline and extracted with methylene chloride. The methylene chloride layer was washed with water, dried over anhydrous sodium sulfate and concentrated under reduced pressure to give a crude enamine. The crude enamine was cyclized by heating at 120° C.–130° C. and then dissolved in methanol. A mixture of this solution and 1.5 g of 10% Palladium on charcoal was vigorously stirred in a hydrogen atomosphere at room temperature until the consumption of hydrogen ceased. The catalyst was filtered off and the filtrate was evaporated in vacuo. The residue was chromatographed on silica gel to give trans 17-oxoeburnane, M.P. 150°–152° C.

EXAMPLE 15

In a similar manner to Example 10, trans ethyl apovincaminate was obtained, M.P. 99.5°–102° C.

IR $\nu_{cm-1}^{film}$: 1725 cm$^{-1}$
NMR $\delta$(CDCl$_3$): 0.73 ppm (3H), 1.37 ppm (3H).

What we claim is:

1. A process for producing a compound of the formula:

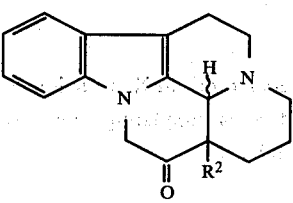

wherein R$^2$ is hydrogen atom or a C$_1$–C$_6$ alkyl group, or a pharmaceutically acceptable acid addition salt there of which comprises heating a compound of the formula:

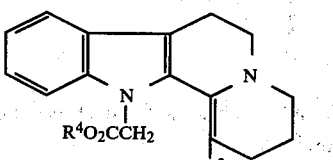

wherein R$^2$ is as defined above and R$^4$ is a C$_1$–C$_6$ alkyl group, followed by hydrogenation employing a platinum or palladium catalyst.

2. A process for producing a compound of the formula:

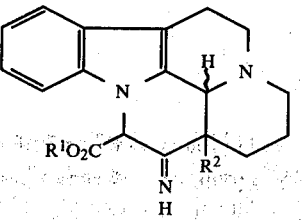

wherein R$^1$ is a C$_1$–C$_6$ alkyl group and R$^2$ is a hydrogen atom or a C$_1$–C$_6$ alkyl group; or a pharmaceutically acceptable acid addition salt thereof, which comprises allowing a compound of the formula:

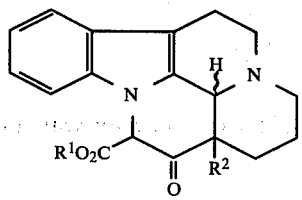

wherein R$^2$ is as defined above, to react with a compound of the formula:

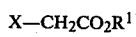

X—CH$_2$CO$_2$R$^1$ wherein R$^1$ is as defined above and X is a halogen atom.

3. A process for producing a compound of the formula:

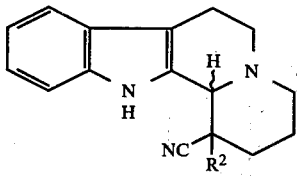

wherein R$^1$ is a C$_1$–C$_6$ alkyl group and R$^2$ is a hydrogen atom or a C$_1$–C$_6$ alkyl group, or a pharmaceutically acceptable acid addition salt thereof, which comprises allowing a compound of the formula:

wherein R$^2$ is as defined above, to react with a compound of the formula:

X—CH$_2$CO$_2$R$^1$ wherein R$^1$ is as defined above and X is a halogen atom and hydrolyzing the resulting compound of the formula:

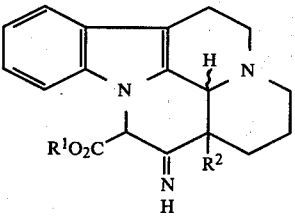

wherein R$^1$ and R$^2$ are each as defined above, in the presence of a mineral acid.

4. A process for producing a compound of the formula:

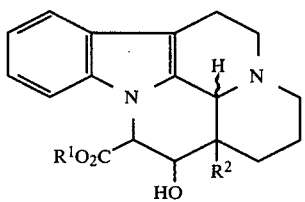

wherein R¹ is a $C_1$-$C_6$ alkyl group and R² is a hydrogen atom or a $C_1$-$C_6$ alkyl group, or a pharmaceutically acceptable acid addition salt thereof, which comprises allowing a compound of the formula:

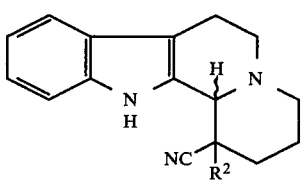

wherein R² is as defined above, to react with a compound of the formula:

$$X-CH_2CO_2R^1$$

wherein R¹ is as defined above and X is a halogen atom, hydrolyzing the resulting compound of the formula:

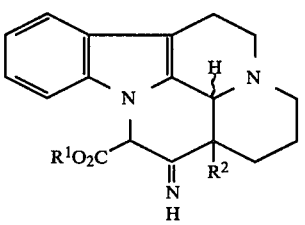

wherein R¹ and R² are each as defined above, in the presence of a mineral acid and reducing the resulting compound of the formula:

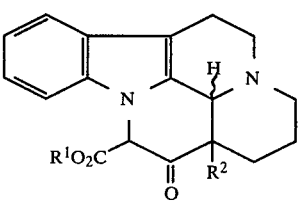

wherein R¹ and R² are each as defined above, with a metal hydride.

5. A process for producing a compound of the formula:

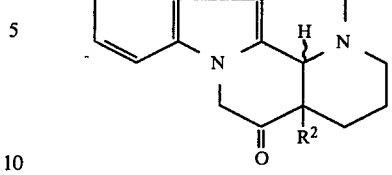

wherein R¹ is a $C_1$-$C_6$ alkyl group and R² is a hydrogen atom or a $C_1$-$C_6$ alkyl group, or a pharmaceutically acceptable acid addition salt thereof, which comprises allowing a compound of the formula:

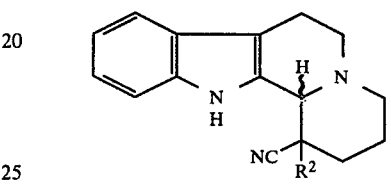

wherein R² is as defined above, to react with a compound of the formula:

$$X-CH_2CO_2R^1$$

wherein R¹ is as defined above and X is a halogen atom and hydrolyzing and decarboxylating the resulting compound of the formula:

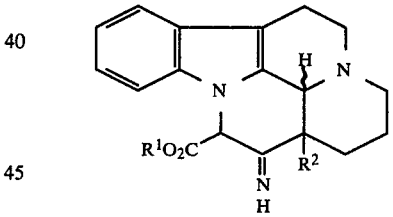

wherein R¹ and R² are each as defined above, in the presence of a mineral acid.

6. A process for producing a compound of the formula:

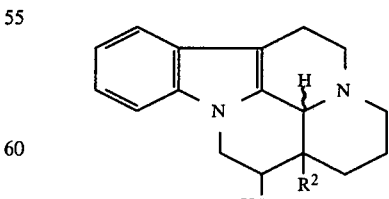

wherein R¹ is a $C_1$-$C_6$ alkyl group and R² is a hydrogen atom or a $C_1$-$C_6$ alkyl group, or a pharmaceutically acceptable acid addition salt thereof, which comprises allowing a compound of the formula:

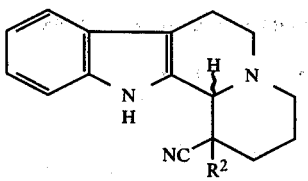

wherein $R^2$ is as defined above, to react with a compound of the formula:

X—CH$_2$CO$_2$R$^1$ wherein $R^1$ is as defined above and X is a halogen atom, hydrolyzing and decarboxylating the resulting compound of the formula:

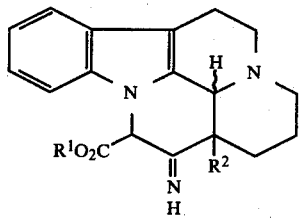

wherein $R^1$ and $R^2$ are each as defined above, in the presence of a mineral acid and reducing the resulting compound of the formula:

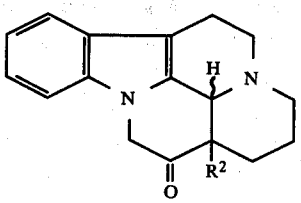

wherein $R^1$ and $R^2$ are each as defined above, with a metal hydride.

7. A process for producing a compound of the formula:

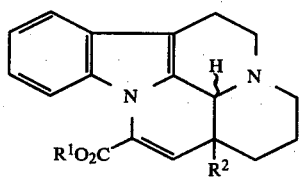

wherein $R^1$ is a $C_1$–$C_6$ alkyl group and $R^2$ is a hydrogen atom or a $C_1$–$C_6$ alkyl group; or a pharmaceutically acceptable acid addition salt thereof, which comprises allowing a compound of the formula:

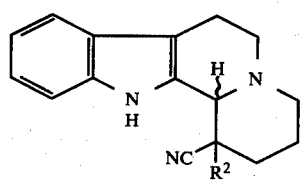

wherein $R^2$ is a hydrogen atom or a $C_1$–$C_6$ alkyl group, to react with a compound of the formula:

X—CH$_2$CO$_2$R$^1$ wherein X is a halogen atom and $R^1$ is a $C_1$–$C_6$ alkyl group, followed by hydrolysis of the imine group in the presence of a mineral acid and metal hydride reduction of the carbonyl group, to form a compound of the formula:

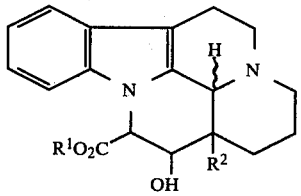

wherein $R^1$ and $R^2$ are each as defined above and then heating the resulting compound in the presence of a metal hydride, metal amide or metal alkoxide.

8. A process for producing a compound of the formula:

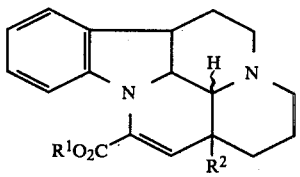

wherein $R^1$ is a $C_1$–$C_6$ alkyl group and $R^2$ is a hydrogen atom or a $C_1$–$C_6$ alkyl group; or a pharmaceutically acceptable acid addition salt thereof which comprises allowing a compound of the formula:

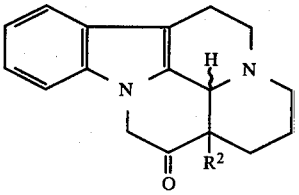

wherein $R^2$ is a hydrogen atom or a $C_1$–$C_6$ alkyl group, to react with a dialkylcarbonate, followed by metal hydride reduction, to form a compound of the formula:

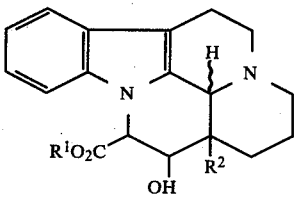

wherein $R^1$ and $R^2$ are each as defined above and then heating the resulting compound in the presence of a metal hydride, metal amide or metal alkoxide.

9. A process according to any one of claims 3 through 6, or 7 wherein the mineral acid is hydrochloric acid, sulfuric acid or phosphoric acid.

10. A process according to any one of claims 4, 6, 7, or 8 wherein the metal hydride is sodium borohydride or calcium borohydride.

11. A process as claimed in claim 7 wherein $R^2$ is an ethyl group.

12. A process as claimed in claim 8 wherein $R^2$ is an ethyl group.

* * * * *

UNITED STATES PATENT AND TRADEMARK OFFICE
CERTIFICATE OF CORRECTION

PATENT NO. : 4,316,028
DATED : February 16, 1982
INVENTOR(S) : Junki KATSUBE et al It is certified that error appears in the above—identified patent and that said Letters Patent is hereby corrected as shown below:

On the first page of the patent, under item

[30]    Foreign Application Priority Data add the following fourth priority application -- Oct. 4, 1979 [JP]    Japan ......... 54-128498    --

Signed and Sealed this

Tenth Day of August 1982

[SEAL]

Attest:

GERALD J. MOSSINGHOFF

*Attesting Officer*    *Commissioner of Patents and Trademarks*